United States Statutory Invention Registration [19]

[11] Reg. Number: H4

Cullen [45] Published: Dec. 3, 1985

[54] PROCESSS FOR THE PREPARATION OF IMINODIACETONITRILE

[75] Inventor: Barry A. Cullen, Amherst, N.H.

[73] Assignee: W. R. Grace & Co., New York, N.Y.

[21] Appl. No.: 732,791

[22] Filed: May 10, 1985

Related U.S. Application Data

[63] Continuation of Ser. No. 668,118, Nov. 5, 1984, which is a continuation-in-part of Ser. No. 423,510, Sep. 27, 1982, abandoned.

[51] Int. Cl.[3] ..... C07C 121/43; C07C 121/44

[52] U.S. Cl. ..... 260/465.5 A

[58] Field of Search ..... 260/465.5 A

*Primary Examiner*—Teddy S. Gron

*Attorney, Agent, or Firm*—Ronald A. Bleeker

[57] ABSTRACT

Iminodiacetonitrile is prepared in a batch process comprising the addition of HCN to an acidified solution of hexamethylenetetramine while maintaining the resulting solution at a temperature of 20°-90° C. by cooling and at a pH of 5.5-6.5 by the addition of formaldehyde.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESSS FOR THE PREPARATION OF IMINODIACETONITRILE

This is a continuation of application Ser. No. 668,118, filed Nov. 5, 1984, which is a continuation-in-part of application Ser. No. 423,510, filed Sept. 27, 1982, now abandoned.

BACKGROUND OF THE INVENTION

The present invention is directed to a process for the preparation of iminodiacetonitrile (IDAN), a valuable intermediate used to prepare compounds such a iminodiacetic acid.

It is well known that IDAN can be obtained by reacting hexamethylenetetramine (HMTA) or its precursors (ammonia and formaldehyde) with HCN. Eschweiler, *Ann.*, 278, 229-239 (1894); Dubsky et al., *Ber.*, 54, 2659 (1921).

In 1957, Miller U.S. Patent No. 2,794,044 disclosed that IDAN could be prepared in a batch reaction having a yield of about 65% by reacting three moles of HCN, two moles of ammonia, and two moles of formaldehyde in an aqueous solution having a pH of 5.5-6.5. Subsequently, in 1965, Saunders U.S. Pat. No. 3,167,580 taught that IDAN could be produced from the same three reactants in a continuous process carried out at a pH of 7-9 if different mole ratios were used.

It is also known that IDAN can be prepared by the reaction of HMTA and HCN in an acidic aqueous medium. In a batch operation, this reaction can be represented as follows:

$$(CH_4)_6N_4 + 6HCN \xrightarrow{H^+} NH_4^+ + 3HN(CH_2CN)_2$$

It can be seen that this reaction only succeeds in converting three of the four nitrogens in the HMTA to the desired product, with the remaining nitrogen forming ammonium by-products. The formation of these by-products requires that the acidic pH of the reaction must be maintained by the addition of acid to the reaction mixture. The actual product is thus a slurry of IDAN crystals in a liquor containing dissolved IDAN, HCN, and other organic and ammonium by-products. These by-products either cannot be separated (which means the liquor cannot be recycled and requires costly effluent treatment) or can only be separated with difficulty. An example is Stutts U.S. Pat. No. 3,412,137 which teaches a batch process for preparing IDAN by reacting an aqueous solution of HMTA with HCN in an aqueous medium buffered with a weak acid (preferably acetic or phosphoric acid) to a pH of 5.5-6.5 at temperatures of 0°-75° C. Cullen U.S. Pat. No. 3,993,681 teaches a batch process wherein HMTA and HCN are reacted in an aqueous solution in the presence of a strong acid at pH 5.5-6.5 and temperatures of 30°-70° C. while maintaining an excess of HCN in the reaction mix. Koenig Canadian Patent No. 684,850 prepares IDAN by reacting HMTA (or its precursors) with HCN in aqueous solution and then acidifying with a strong mineral acid. Similarly, the recent Suchland et al. U.S. Pat. No. 4,307,037 reacts HMTA with HCN in an aqueous medium initially having a pH of 5.5-7.5 and then further acidifying the reaction mixture by 0.5-3.5 pH units by the addition of an acid (preferability sulfuric) at a temperature of 30°-90° C. All of the foregoing references teach batch operations, use the foregoing mole ratio of six moles of HCN to one mole of HMTA, are conducted in an aqueous medium whose acidic pH is maintained by the addition of acid, and are conducted at fairly low temperatures. In contrast, Philbrook et al. U.S. Pat. No. 3,886,198 discloses a continuous process for the preparation of IDAN by passing a mixture of HMTA, HCN, and a strong acid through a tubular reactor. This continuous process differs from the batch process in that it involves five to seven moles of HCN per mole of HMTA and must be operated at a higher temperature, which is an additional disadvantage.

An alternate route to IDAN involves the use of glycolonitrile as a reactant. This is disclosed in Gaudette et al. U.S. Pat. No. 3,904,668 wherein an aqueous mixture of HMTA, HCN, and glycolonitrile is continuously passed through a tubular reactor. The process has the advantage of converting all four nitrogens in the HMTA to the IDAN product.

A more recently developed route involves the addition of formaldehyde, rather than an acid, to maintain the pH of the reaction mixture. A continuous process of this type for the formation of IDAN by the reaction of HMTA, HCN, and formaldehyde is shown in Gaudette et al. U.S. Pat. No. 3,988,360. Like the Gaudette '668 patent, the process theoretically converts all four nitrogens in the HMTA to IDAN, with no formation of ammonium by-product:

$$(CH_2)_6N_4 + 8HCN + 2HCHO \rightarrow 4HN(CH_2CN)_2 + 2H_2O$$

However, because it must be operated at higher temperatures, usually 130°-150° C., this continuous process has been found to suffer from low yields caused by the formation of by-products. It has now been found that batch operation of the reaction described in the Gaudette '360 patent results in a significantly higher yield of a pure, colorless IDAN. It is believed that the reason for this result is the lower temperature at which this batch process may be operated. In contrast, the higher temperature of a continuous process such as that described in the Gaudette '360 patent favors the occurrence of side-reactions which result in the formation of undesirable by-products and color bodies.

In short, the present invention's use of formaldehyde instead of acid as well as the use of lower temperatures both tend to minimize the formation of undesirable by-products and give a higher yield of IDAN.

SUMMARY OF THE INVENTION

A pure, colorless iminodiacetonitrile is prepared in high yields in a batch process comprising the addition of HCN to an acidified solution of HMTA while the resulting solution is maintained at a temperature of 20°-90° C. by cooling and the pH at 5.5-6.5 by the addition of formaldehyde.

DETAILED DESCRIPTION OF THE INVENTION

IDAN is produced by the reaction of HMTA, HCN, and formaldehyde according to the following equation:

$$(CH_2)_6N_4 + 8HCN + 2HCHO \rightarrow 4HN(CH_2CN)_2 + 2H_2O$$

This reaction has the advantage that all four nitrogens of the HMTA are converted to the IDAN product, unlike prior processes wherein only three of the nitrogens were converted:

$$(CH_2)_6N_4 + 6HCN \xrightarrow{H^+} 3HN(CH_2CN)_2 + NH_4^+$$

It is believed that in the reaction of the present invention the additional formaldehyde reacts with the ammonium ion in situ to form hexamine or a hexamine precursor which is subsequently converted to IDAN by reaction with the HCN. The minimization of undesirable ammonium by-products not only increases the IDAN yield but also avoids the need for costly effluent treatment.

In carrying out the process of the present invention, an aqueous solution of HMTA (1.0M) is first preneutralized with acid to a pH of 5.5–6.5 and the temperature adjusted to 0°–60° C. HCN (8–10M) is then added to this solution either all at once or over a period of time (up to about four hours). The temperature of the resulting solution is maintained between about 20° C. and about 90° C. with cooling and the pH is maintained between about 5.5–6.5 with the addition of aqueous formaldehyde (2–4M) over a period of from about one to about ten hours. The crystalline IDAN product can then be isolated from the aqueous solution after cooling (e.g. by decantation, filtration, or centrifugation). Alternatively, the IDAN product can be saponified to form dialkali metal iminodiacetate, by-product ammonia (which is recoverable), and a by-product alkali metal salt.

The initial pre-neutralization of the aqueous HMTA solution can be carried out with a variety of acids, ranging from weak to strong. Sulfuric, formic, and acetic acid were all used in actual examples but it should be apparent that other acids could readily be substituted. Although sulfuric is preferred for economic reasons, no change in IDAN recovery (about 81%) occurred when formic acid was substituted on a 1:1 equivalent basis for sulfuric. With acetic acid, a slightly lower recovery (76.2%) was obtained when an equivalent amount of acetic was substituted for sulfuric. However, when 1.9 equivalents of acetic acid were used the pH decreased and a recovery of 81.2% was obtained.

Table I shows the results of a series of experiments carrying out the process of the invention. The following experimental procedure was used in each run: A one liter three-necked Morton flask equipped with pH probe, thermometer, condenser, and mechanical stirrer was charged with 1.0M of HMTA (duPont Tech. grade crystal) as a 32.2% aqueous solution. This was neutralized with acid to a pH in the range of 5.5 to 6.0 depending on the run. Hydrogen cyanide (8.15M) was added over 20 minutes after the temperature had been adjusted to 25°–27° C. The temperature profile (Table II) was followed by heating or cooling the flask. The pH was maintained within the desired range by carefully adding an aqueous solution of 44% formaldehyde in small portions. Readings of the quantity of formaldehyde used were taken every 10 minutes for the first 11 runs. Thereafter, the average formaldehyde requirement to maintain pH over 10 minutes was calculated and the results used as a guideline in the later runs. In adding the formaldehyde, there was usually a lag of several minutes before a pH reduction was noted, especially at the lower temperatures.

It can be seen that in the later runs (after the amount of formaldehyde necessary to maintain a pH was established) recovery of IDAN became consistent at about 81% (based on 4M of IDAN per mole of HMTA). This is about 20–25% better recovery than that achieved in the standard acid-buffered reaction.

TABLE I

| Run # | Acid Eq. | Neutral pH | Reaction pH | Formaldehyde Usage, M | IDAN % Yield | % YLD. on N avail. | % YLD $CH_2O$ |
|---|---|---|---|---|---|---|---|
| 1 | 0.326[1] | 6.00 | 5.60[4] | 2.136 | 77.5 | 84.4 | 76.2 |
| 2 | 0.326[1] | 5.92 | 5.60[4] | 3.970 | 75.6 | 82.3 | 60.7 |
| 3 | 0.410[1] | 5.97 | 5.75[4] | 2.039 | 78.7 | 87.7 | 78.3 |
| 4 | 0.359[1] | 5.80 | 5.85[4] | 1.935 | 73.0 | 80.2 | 73.6 |
| 5 | 0.396[1] | 5.83 | 5.65[4] | 1.113 | 81.5 | 90.5 | 91.7 |
| 6 | 0.688[1] | 5.56 | 5.60[4] | 1.168 | 78.3 | 94.6 | 87.4 |
| 7 | 0.500[1] | 5.80 | 5.60[4] | 1.850 | 80.7 | 92.2 | 82.2 |
| 8 | 0.408[1] | 5.89 | 5.60[4] | Spilled | 83.6 | 93.1 | — |
| 9 | 0.408[1] | 5.79 | 5.60[4] | 2.141 | 75.4 | 84.0 | 74.1 |
| 10 | 0.408[1] | 5.88 | 5.60[4] | 2.397 | 88.8 | 98.9 | 84.6 |
| 11 | 0.396[1] | 5.85 | 5.65[4] | 3.714 | Sticky | — | — |
| 12 | 0.456[1] | 5.83 | 5.65[4] | 2.115 | 81.6 | 92.1 | 80.4 |
| 13 | 0.388[1] | 5.90 | 5.64–5.90 | 1.710 | 80.2 | 88.8 | 83.2 |
| 14 | 0.388[1] | 5.83 | 5.63–6.56 | 1.941 | 80.2 | 88.8 | 80.8 |
| 15 | 0.388[1] | 5.93 | 5.55–5.93 | 2.174 | 80.3 | 88.9 | 78.6 |
| 16 | 0.388[1] | 5.97 | 5.60–5.97 | 2.255 | 80.8 | 89.5 | 78.3 |
| 17 | 0.388[1] | 5.76 | 5.54–4.81 | 2.279 | 81.8 | 90.6 | 79.0 |
| 18 | 0.388[1] | 5.92 | 5.57–5.62 | 2.383 | 81.4 | 90.1 | 77.7 |
| 19 | 0.388[2] | 5.76 | 5.80–5.94 | 2.045 | 81.7 | 90.5 | 81.2 |
| 20 | 0.388[2] | 5.96 | 6.00–6.30 | 1.913 | 76.2 | 84.4 | 77.0 |
| 21 | 0.734[3] | 5.60 | 5.64–5.78 | 1.820 | 81.2 | 99.5 | 83.1 |
| 22 | 0.397[2] | 5.80 | 5.65–5.80 | 1.956 | 81.1 | 90.0 | 81.5 |

TABLE I-continued

| Run # | Acid Eq. | Neutral pH | Reaction pH | Formaldehyde Usage, M | IDAN % Yield | % YLD. on N avail. | % YLD $CH_2O$ |
|---|---|---|---|---|---|---|---|
| | | | | Average of 13,14,15,16,18,19 & 22 | | | |

[1]$H_2SO_4$
[2]$HCO_2H$
[3]$CH_3CO_2H$
[4]Set Point

TABLE II

| Time (Min.) | Temp. (°C.) |
|---|---|
| 0 | 28 |
| 10 | 26 |
| 20 | 23.5 |
| 30 | 21 |
| 40 | 21.8 |
| 50 | 22.5 |
| 60 | 23.5 |
| 70 | 25.8 |
| 80 | 27 |
| 90 | 28 |
| 100 | 29 |
| 110 | 30 |
| 120 | 43 |
| 130 | 54 |
| 140 | 66 |
| 150 | 60 |
| 160 | 60 |
| 170 | 60 |
| 180 | Vacuum cool to 20° C. over 1 hr. |

While the invention has been described in connection with certain preferred conditions, equipment, and embodiments, it is not intended to limit the invention to the particular form set forth, but, on the contrary, it is intended to cover such alternatives, modifications, and equivalents as defined by the appended claims.

I claim:

1. A batch process for the producton of iminodiacetonitrile which comprises:

(a) pre-neutralizing a first aqueous solution of hexamethylenetetramine to a pH between about 5.5 and about 6.5 with an acid and adjusting the temperature to between about 0° C. to about 60° C.;

(b) forming a second aqueous solution by adding HCN to the first aqueous solution while maintaining the temperature between about 20° C. and about 90° C. with cooling and the pH between about 5.5 and 6.5 by the addition of formaldehyde; and (c) cooling the second aqueous solution and then recovering the iminodiacetonitrile product.

2. A process according to claim 1 in which the acid used to pre-neutralize the first aqueous solution is selected from the group consisting of sulfuric, formic, and acetic acids.

3. A process according to claim 1 in which the HCN is added to the second aqueous solution over a period up to about four hours.

4. A process according to claim 1 in which the formaldehyde is added to the second aqueous solution over a period of between about one and about ten hours.

5. A process according to claim 1 in which the temperature of the second aqueous solution is maintained between about 20° C. and about 75° C.

6. A process according to claim 1 in which the pH of the first aqueous solution is maintained between about 5.8 and about 6.0.

7. A process according to claim 1 in which the pH of the second aqueous solution is maintained between about 5.5 and 6.5.

8. A process according to claim 1 in which for each mole of hexamethylenetetramine about eight moles of HCN and about two moles of formaldehyde are used.

* * * * *